(12) United States Patent
Liang et al.

(10) Patent No.: US 10,717,068 B2
(45) Date of Patent: Jul. 21, 2020

(54) METHANE OXIDATIVE COUPLING WITH LA—CE CATALYSTS

(71) Applicant: SABIC Global Technologies B.V., Bergen op Zoom (NL)

(72) Inventors: Wugeng Liang, Sugar Land, TX (US); Sagar Sarsani, Sugar Land, TX (US); David West, Sugar Land, TX (US); James Lowrey, Sugar Land, TX (US); Aghaddin Mamedov, Sugar Land, TX (US); Istvan Lengyel, Sugar Land, TX (US)

(73) Assignee: SABIC GLOBAL TECHNOLOGIES, Bergen op Zoom (NL)

( * ) Notice: Subject to any disclaimer, the term of this patent is extended or adjusted under 35 U.S.C. 154(b) by 0 days.

(21) Appl. No.: 15/579,332

(22) PCT Filed: May 2, 2016

(86) PCT No.: PCT/US2016/030373
§ 371 (c)(1),
(2) Date: Dec. 4, 2017

(87) PCT Pub. No.: WO2016/200503
PCT Pub. Date: Dec. 15, 2016

(65) Prior Publication Data
US 2018/0353940 A1      Dec. 13, 2018

Related U.S. Application Data

(60) Provisional application No. 62/172,403, filed on Jun. 8, 2015.

(51) Int. Cl.
*B01J 23/10*      (2006.01)
*B01J 35/00*      (2006.01)
(Continued)

(52) U.S. Cl.
CPC ............... *B01J 23/10* (2013.01); *B01J 21/08* (2013.01); *B01J 23/002* (2013.01); *B01J 35/002* (2013.01);
(Continued)

(58) Field of Classification Search
CPC .... B01J 2523/3706; B01J 23/20; B01J 21/08; B01J 23/02; B01J 35/002; B01J 35/0046; B01J 37/08
See application file for complete search history.

(56) References Cited

U.S. PATENT DOCUMENTS

| 4,997,802 A | 3/1991 | Matsuura et al. |
| 5,105,053 A | 4/1992 | Jacobson et al. |

(Continued)

FOREIGN PATENT DOCUMENTS

| CN | 1045198 | 9/1999 |
| CN | 101664680 | 3/2010 |

(Continued)

OTHER PUBLICATIONS

Bhasin, et al., "Feasability of Ethylene Synthesis Via Oxidative Coupling of Methane," *Studies in Surface Science and Catalysis*, 36, pp. 343-357. (1988).

(Continued)

*Primary Examiner* — James A Fiorito
(74) *Attorney, Agent, or Firm* — Norton Rose Fulbright US LLP (57) ABSTRACT

A metal oxide catalyst capable of catalyzing an oxidative coupling of methane reaction is described. The metal oxide catalyst includes a lanthanum (La) cerium (Ce) metal oxide and further including a lanthanum hydroxide ($La(OH)_3$) crystalline phase. The catalyst is capable of catalyzing the production of $C_2$+ hydrocarbons from methane and oxygen. Methods and systems of using the metal oxide catalyst to (Continued)

produce C₂+ hydrocarbons from a reactant gas are also described.

20 Claims, 7 Drawing Sheets

(51) Int. Cl.
*B01J 21/08* (2006.01)
*B01J 23/00* (2006.01)
*B01J 37/08* (2006.01)
*C07C 2/84* (2006.01)

(52) U.S. Cl.
CPC .......... *B01J 35/0046* (2013.01); *B01J 37/08* (2013.01); *C07C 2/84* (2013.01); *B01J 2523/3706* (2013.01); *B01J 2523/3712* (2013.01); *C07C 2523/10* (2013.01)

(56) References Cited

U.S. PATENT DOCUMENTS

| | | | |
|---|---|---|---|
| 5,411,927 | A | 5/1995 | Choudhary et al. |
| 8,399,726 | B2 | 3/2013 | Chinta et al. |
| 8,796,497 | B2 | 8/2014 | Chinta et al. |
| 8,912,381 | B2 | 12/2014 | Chinta et al. |
| 2010/0331595 | A1 | 12/2010 | Chinta et al. |
| 2012/0041246 | A1 | 2/2012 | Scher et al. |
| 2013/0023709 | A1 | 1/2013 | Cizeron et al. |
| 2013/0165728 | A1 | 6/2013 | Zurcher et al. |
| 2013/0225884 | A1 | 8/2013 | Weinberger et al. |
| 2014/0107385 | A1 | 4/2014 | Schammel et al. |
| 2014/0121433 | A1 | 5/2014 | Cizeron et al. |
| 2014/0171707 | A1 | 6/2014 | Nyce et al. |
| 2014/0274671 | A1 | 9/2014 | Schammel et al. |
| 2015/0087875 | A1 | 3/2015 | Zurcher et al. |

FOREIGN PATENT DOCUMENTS

| | | |
|---|---|---|
| CN | 103350002 | 10/2013 |
| EP | 582004 | 1/1997 |

OTHER PUBLICATIONS

Bhattacharya, et al., "Catalytic Oxidative Coupling of Methane on Metal Oxides: I. Effect of Oxidation State of Bismuth and Reversibility of Lattice Oxygen on Activity in Barium-Lanthanum-Bismuth Oxides," *Applied Catalysis A: General*, 85(2), pp. 135-145. (1992).

Dedov, et al., "Oxidative Coupling of Methane Catalyzed by Rare Earth Oxides: Unexpected Synergistic Effect of the Oxide Mixtures," *Applied Catalysis A: General*, 245(2), pp. 209-220. (2003).
Djaidja, et al., "Oxidative Transformation of Methane Over Nickel Catalysts Supported on Rare-Earth Metal Oxides," *Catalysis Today*, 61(1-4), pp. 303-307. (2000).
Ferreira, et al., "Ce-Doped $La_2O_3$ Based Catalyst for the Oxidative Coupling of Methane," *Catalysis Communications*, 42, pp. 50-53. (2013).
Hou, et al., "Structure Sensitivity of $La_2O_3$ Catalysts in the Oxidative Couple of Methane," *ACS Catalysis*, 5(3), pp. 1663-1674. (2015).
Hu, et al., "Dual Catalyst Bed for Oxidation of $CH_4$ Simultaneously to $C_2H_4$ and Syngas," *AIChE Journal*, 53(11), pp. 2925-2931. (2007).
International Preliminary Report on Patentability Issued in Corresponding PCT Application No. PCT/US2016/030384, dated Jun. 19, 2017.
International Search Report and Written Opinion Issued in Corresponding PCT Application No. PCT/US2016/030373, dated Aug. 30, 2016.
Makhlin, et al., "Oxidative Dimerization of Methane: Kinetics, Mathematical Modeling, and Optimization with La/Ce Catalytics," *Russian Journal of General Chemistry*, 79(9), pp. 2016-2023. (2009).
Noon, et al. "Oxidative Couple of Methane by Nanofiber Catalysts," *ChemCatChem Catalysis*, 5. pp. 146-149. (2013).
Noon, et al., "Oxidative Coupling of Methane with $La_2O_3$—$CeO_2$ Nanofiber Fabrics: A Reaction Engineering Study," *Journal of Natural Gas Science and Engineering*, 18, pp. 406-411. (2014).
Sadjadi, et al., "Feasibility Study of the $Mn\_Na_2WO_4/SiO_2$ Catalytic System for the Oxidative Coupling of Methane in a Fluidized-Bed Reactor," *Catalysis Science & Technology*, 5(2), pp. 942-952. (2014).
Salerno-Paredes, "Optimal Synthesis Downstream Processes Using the Oxidative Coupling of Methane Reaction," Master Thesis, Technischen Universitat Berlin, Oct. 19, 2012.
Taylor, et al., "Lanthanum Catalysts for Methane Oxidative Coupling: A Comparison of the Reactivity of Phases," *Industrial and Engineering Chemistry Research*, 30(5), pp. 1016-1023. (1991).
Wang, et al., "Low-Temperature Selective Oxidation of Methane to Ethane and Ethylene over $BaCO_3/La_2O_3$ Catalysts Prepared by Urea Combustion Method," *Catalysis Communications*, 7(2), pp. 59-63. (2006)
Wang, et al., "Oxidative Coupling of Methane and Oxidative Dehydrogenation of Ethane Over $La_2O_3$ Nano-Catalyst at Low Temperature," *Petrochemical Technology*, 36(5), pp. 437-440. (2007).
Zhang, et al., "Oxidative Coupling of Methane Using Microwave Dielectric Heating," *Applied Catalysis A: General*, 249(1), pp. 151-164. (2003).

METHANE OXIDATIVE COUPLING WITH LA—CE CATALYSTS

CROSS REFERENCE TO RELATED APPLICATIONS

This application is a national phase application under 35 U.S.C. § 371 of International Application No. PCT/US2016/030373 filed May 2, 2016, which claims the benefit of priority of U.S. Provisional Patent Application No. 62/172,403, filed Jun. 8, 2015. The entire contents of each of the above-referenced disclosures are specifically incorporated herein by reference without disclaimer.

BACKGROUND OF THE INVENTION

A. Field of the Invention

The invention generally concerns the use of lanthanide-cerium bulk metal oxide catalysts that are capable of producing $C_{2+}$ hydrocarbons from methane ($CH_4$) and oxygen ($O_2$). In particular, the bulk metal oxide catalysts include a lanthanum hydroxide ($La(OH)_3$) crystalline phase.

B. Description of Related Art

Due to advancements in technology, more and more shale reservoirs are being produced, which in turn gives rise to more and more natural gas being produced. Natural gas is a naturally occurring mixture of hydrocarbon gases. Natural gas includes methane and contains up to about twenty percent concentration of higher hydrocarbons such as ethane and small quantities of impurities such as carbon dioxide and hydrogen sulfide. While natural gas is an abundant hydrocarbon resource it has a low economic value as compared to more valued hydrocarbons having a carbon number of 2 or greater (e.g., ethylene, ethane, propane, etc.), which can be used to produce a wide range of products. For example, ethylene is a key raw material of the petrochemical industry for making polyethylene, ethylene oxide and other petrochemical products. Many of these products are used as to produce a wide range of products such as break-resistant containers and packaging materials. For industrial scale applications, ethylene is currently produced by steam or catalytic cracking of products obtained from distillation gaseous or light hydrocarbons, which include ethane and higher hydrocarbons. The resulting product is subjected to separation processes to remove ethylene.

Methane can be used to produce ethane and/or ethylene by oxidative coupling of the methane with itself. Extensive research and development has been devoted to the technology of oxidative coupling, however, no process has been successfully commercialized. One of the key challenging issues is the high reaction temperature required to make the reaction proceed. The high temperatures are required because the dissociation strength (bond dissociation enthalpies) of the tetrahedral C—H bonds in methane is 435 kilojoules per mole (kJ/mol), which makes it less reactive, and difficult to undergo oxidative conversion to form ethylene. The oxidative coupling of the methane is represented by the following equations:

$$2CH_4 + O_2 \rightarrow C_2H_4 + 2H_2O \quad \Delta H = -34 \text{ kcal/mol} \tag{I}$$

$$2CH_4 + \tfrac{1}{2}O_2 \rightarrow C_2H_4 + H_2O \quad \Delta H = -21 \text{ kcal/mol} \tag{II}$$

As shown in Equations (I) and (II), oxidative conversion of methane to ethylene is exothermic. Excess heat produced from these reactions can push conversion of methane to carbon monoxide and carbon dioxide rather than the desired $C_2$ hydrocarbon product:

$$CH_4 + 1.5O_2 \rightarrow CO + 2H_2O \quad \Delta H = -103 \text{ kcal/mol} \tag{III}$$

$$CH_4 + 2O_2 \rightarrow CO_2 + 2H_2O \quad \Delta H = -174 \text{ kcal/mol} \tag{IV}$$

The excess heat from the reactions in Equations (III) and (IV) further exasperate this situation, thereby substantially reducing the selectivity of ethylene production when compared with carbon monoxide and carbon dioxide production.

Many attempts to lower the ignition and reaction temperatures have involved the use of catalysts, however, temperatures of higher than 750° C. are still necessary to achieve satisfactory results. In conventional methods, the reactant feed is heated to the reaction temperature (e.g., greater than 750° C.) in a furnace (e.g., a natural gas furnace) before entering the reactor. In order to heat the mixture to the required temperature, the furnace temperature has to be higher than the required temperature. Thus, a high temperature furnace is needed and a substantial amount of energy (e.g., electricity derived from hydrocarbons) or fuel is required to generate the heat (See, for example, Salerno, Ph.D. Thesis, Technical University of Berlin, page 42, FIG. 2.4). Furthermore, operation at such high temperature requires special materials for reactor construction. Additionally, at high temperatures agglomeration (coking) of methane oxidative coupling catalysts can take place. Such agglomeration can cause deactivation of the catalyst.

There have been many attempts to provide improved catalysts to promote the oxidative coupling of methane. For example, US 2013/0023709 to Cizeron et al., US 2014/0107385 and US 2014/0274671 to Schammel et al., and US 20140171707 to Nyce et al. each describe systems and methods that use nanowire metal oxide catalysts. The catalysts include elements from Groups 1-7 and dopants from Groups 1-16, lanthanides, actinides, or combinations thereof. These catalysts suffer in that they are made using biological templates and multi-step methods, which can increase the overall cost for producing the catalyst. Chinese Patent Publication No. CN1045198C describes a catalyst that includes a basic metal hydroxide oxide compound (MOOH) where M is at least one metal of Group IIB of the Periodic Table. These catalysts suffer in that they require a multistep heat treatment process and must be sealed after preparation. These catalysts also suffer in that they produce low amounts of $C_2$ hydrocarbons (11-13%) at 300° C.

SUMMARY OF THE INVENTION

The present application provides a solution to the problems associated with the elevated ignition and reaction temperatures used for oxidative coupling of methane to produce $C_2+$ hydrocarbons. In one non-limiting embodiment, the solution resides in a lanthanum-cerium (La—Ce) oxide catalyst that includes a lanthanum hydroxide ($La(OH)_3$) crystal phase. It has been surprisingly found that when the molar ratio of La to Ce is greater than 1, the $La(OH)_3$ crystalline phase was present in the crystal lattice of the catalyst. Still further, the catalyst is capable of igniting the reactant mixture at lower temperatures (e.g., 700° C. or less). Thus, the reactant mixture does not need to be heated to high temperatures prior to entering the reactor, which results in a more energy efficient process (e.g., less fuel needs to be burned to heat a furnace positioned prior to the reactor). Further, the catalyst of the present invention is stable under atmospheric conditions and is capable of catalyzing the oxidative coupling of methane to produce $C_2+$ hydrocarbons with high selectivity.

In a particular aspect of the invention, a metal oxide catalyst capable of catalyzing an oxidative coupling of methane reaction is described. The metal oxide catalyst includes a lanthanum (La) cerium (Ce) metal oxide and a lanthanum hydroxide $(La(OH)_3)$ crystalline phase, and the metal oxide catalyst is capable of catalyzing the production of $C_2+$ hydrocarbons from methane and oxygen. The molar ratio of La to Ce in the catalyst can be from $1<La:Ce\leq30$ (e.g., $5<La:Ce\leq30$, and $5<La:Ce\leq15$). The catalyst is crystalline in form and the La and Ce are incorporated into the crystal lattice structure. At La to Ce molar ratios of greater than 1, the $La(OH)_3$ crystalline phase is also present in the crystal lattice of the catalyst. In some aspects of the invention, the metal oxide catalyst is a bulk metal catalyst. The metal oxide catalyst is capable of catalyzing the production of $C_2+$ hydrocarbons from methane and oxygen at a temperature of less than 1000° C., preferably 300° C. to less than 700° C., more preferably 400° C. to 550° C., and most preferably 400° C. to 525° C. Under reaction conditions including a temperature of 450° C. to 500° C. at a methane/oxygen ratio equal to 7.4 ($CH_4/O_2=7.4$), the metal oxide catalyst can have a $C_2+$ hydrocarbon selectivity of at least 60%, 60% to 80%, or 60% to 70% and an oxygen ($O_2$) conversion of at least 90%. When the metal oxide catalyst is contacted with a reactant feed that includes methane and an oxygen containing gas (e.g., air, oxygen, oxygen enriched air, or combinations thereof) at a desired temperature (e.g., an average temperature of less than 1000° C., preferably 300° C. to less than 700° C., preferably 275° C. to less than 700° C., more preferably 300° C. to 550° C., and most preferably 300° C. to 450° C. at least a portion of the methane in the reactant feed can be formed into $C_2+$ hydrocarbons.

In another aspect of the invention, a method of producing $C_2+$ hydrocarbons from an oxidative coupling of methane reaction is described. The method includes contacting a reactant feed that includes methane and an oxygen containing gas with any one of the metal oxide catalysts of described above or throughout the specification under conditions sufficient to produce a first product gas stream that includes $C_2+$ hydrocarbons. Reaction conditions can include an average temperature of less than 1000° C., preferably 275° C. to less than 700° C., more preferably 300° C. to 550° C., and most preferably 300° C. to 450° C. The methane to oxygen ($CH_4/O_2$) ratio can be less than 10, preferably less than 7 and more preferably less than 4. The gas hourly space velocity (GHSV) 500 hr$^{-1}$ or more, 1000 hr$^{-1}$ or more, more 10,000 hr$^{-1}$ or more, or 50,000 hr$^{-1}$ or more. The reaction can be operated under atmosphere pressure and it can also be operated under elevated pressure. In some embodiments, the reactant feed is heated to a temperature less than 700° C., preferably 275° C. to less than 700° C., more preferably 300° C. to 550° C., and most preferably 300° C. to 450° C. At such low temperatures, the catalyst is capable of igniting the reactant feed and maintaining the reaction. Such a method has a $C_2+$ hydrocarbon selectivity of at least 60%, 60% to 80%, or 60% to 70% and an oxygen conversion of at least 90%. In some aspects of the invention, additional catalysts (e.g., 2, 3, 4, 5, etc.) can be positioned downstream of the metal oxide catalyst (e.g., a first catalyst). The first catalyst is positioned near or at the inlet of the reactor and is contacted with the reactant feed prior to contact of the feed with the additional catalyst. In a preferred embodiment, the first catalyst is a La—Ce metal oxide catalyst. The additional catalyst (e.g., a second catalyst) can be any supported, non-supported, or bulk metal catalyst suitable for oxidative coupling of methane. The catalysts can be positioned in catalyst beds that are located in sequence. A non-limiting example of a second catalyst is Mn—$Na_2WO_4$ on $SiO_2$. The second catalyst can have a higher selectivity of $C_2+$ hydrocarbons than the catalyst of the present invention. The first product stream generated using the first catalyst (e.g., metal oxide catalyst of the present invention) can be mixed with additional oxygen and contacted with the second catalyst. Reaction conditions for contacting the first product stream with the second catalyst can include an average temperature of at least 600° C., or 700° C. to 1000° C., 700° C. to 900° C. Over the second catalyst, the methane to oxygen ($CH_4/O_2$) ratio can be less than 10, preferably less than 7 and more preferably less than 4. The gas hourly space velocity (GHSV) can be higher or the same as the GHSV used in the first reaction zone, (e.g., 500 hr$^{-1}$ or more, 1000 hr$^{-1}$ or more, more 10,000 hr$^{-1}$ or more, or 50,000 hr$^{-1}$ or more, 80,000 hr$^{-1}$ or more, preferably higher than 50,000 hr$^{-1}$). The reaction can be operated under atmosphere pressure and it can also be operated under elevated pressure. Over the second catalyst, the method has a $C_2+$ hydrocarbon selectivity is at least 70%, 70% to 90%, or 75% to 80% and an oxygen conversion of at least 90%.

In a particular aspect of the invention, a system for producing $C_2+$ hydrocarbons is described. The system can include an inlet for a reactant feed that includes methane and oxygen, a reaction zone that is configured to be in fluid communication with the inlet, wherein the reaction zone includes any one of the metal oxide catalysts of described throughout the specification (e.g., a first catalyst) and an outlet configured to be in fluid communication with the reaction zone and configured to remove a first product stream that includes $C_2+$ hydrocarbons from the reaction zone. In embodiments when at least two catalysts are used, the second catalyst is positioned downstream of the first catalyst (e.g., La—Ce metal oxide catalyst) and the first product stream obtained from an oxidative coupling of methane reaction between the reactant feed and the metal oxide catalyst is contacted with the second catalyst to produce a second product stream that includes $C_2+$ hydrocarbons. Such a system produces $C_2+$ hydrocarbons in the second product stream in an amount that is greater than the amount of $C_2+$ hydrocarbons in the first product stream (e.g., $C_2+$ hydrocarbon selectivity at least 70%, 80% or 90%) and the conversion of oxygen is at least 90%.

The resulting the $C_2+$ hydrocarbons and water produced from the systems of the invention can be collected in a collection device and/or transported via piping to separation unit. In the separation unit, the $C_2+$ hydrocarbons are separated using known separation techniques, for example, distillation, absorption, membrane technology to produce an ethylene product.

In another aspect of the invention a method of making the metal oxide catalyst of the present invention is described. The method can include obtaining a solution mixture that includes lanthanum and cerium salts such as lanthanum and cerium nitrates, having molar ratio of La to Ce of $1<La:Ce\leq30$, removing the solvent at a temperature of about 120 to 130° C. to obtain a dried mixture, and calcining the dried mixture at an average temperature of 400° C. to 850° C., preferably 500° C. to 700° C., most preferably 600 to 650° C., for a sufficient period of time (e.g., for 3 and 12 hours, preferably 4 and 8 hours) to obtain the metal oxide catalyst described above and throughout the specification.

In the context of the present invention embodiments 1 to 50 are also disclosed. Embodiment 1 is a metal oxide catalyst capable of catalyzing an oxidative coupling of methane reaction, the metal oxide catalyst includes a lanthanum (La) cerium (Ce) metal oxide and further including a lanthanum hydroxide ($La(OH)_3$) crystalline phase, wherein the catalyst is capable of catalyzing the production of $C_2+$ hydrocarbons from methane and oxygen. Embodiment 2 is the metal oxide catalyst of embodiment 1, having a molar ratio of La to Ce of 1<La:Ce<30, 5<La:Ce<30, and 5<La:Ce<15. Embodiment 3 is the metal oxide catalyst of any one of embodiments 1 to 2, wherein the metal oxide catalyst is a bulk metal oxide catalyst. Embodiment 4 is the metal oxide catalyst of any one of embodiments 1 to 3, wherein the metal oxide catalyst is in crystalline form and the La and Ce are incorporated into the crystal lattice structure. Embodiment 5 is the metal oxide catalyst of any one of embodiments 1 to 4, wherein the metal oxide catalyst is capable of catalyzing the production of $C_2+$ hydrocarbons from methane and oxygen at an average temperature of less than 1000° C., preferably 275° C. to less than 700° C., more preferably 400° C. to 550° C., and most preferably 400° C. to 525° C. Embodiment 6 is the metal oxide catalyst of any one of embodiments 1 to 6, wherein the metal oxide catalyst has a $C_2+$ hydrocarbon selectivity of at least 60%, 60% to 80%, or 60% to 70%. Embodiment 7 is the metal oxide catalyst of embodiment 6, wherein the metal oxide catalyst has an $O_2$ conversion of at least 90%. Embodiment 8 is the metal oxide catalyst of any one of embodiments 1 to 7, wherein the metal oxide catalyst is in powdered or particulate form. Embodiment 9 is the metal oxide catalyst of any one of embodiments 1 to 8, wherein the metal oxide catalyst is in contact with a reactant feed that includes methane and an oxygen source. Embodiment 10 is the metal oxide catalyst of embodiment 9, wherein the reactant feed has an average temperature of less than 1000° C., preferably 300° C. to less than 700° C., more preferably 400° C. to 550° C., and most preferably 400° C. to 525° C. Embodiment 11 is the metal oxide catalyst of embodiment 10, wherein at least a portion of the methane in the reactant feed has ignited or has formed into a $C_2+$ hydrocarbon.

Embodiment 12 is a method of producing $C_2+$ hydrocarbons from an oxidative coupling of methane reaction. The method includes contacting a reactant feed that includes methane and an oxygen containing gas with any one of the metal oxide catalysts of embodiments 1 to 11 under conditions sufficient to produce a first product gas stream containing $C_2+$ hydrocarbons. Embodiment 13 is the method of embodiments 12, wherein the oxidative coupling of methane reaction occurs at an average temperature of less than 1000° C., preferably 275° C. to less than 700° C., more preferably 400° C. to 550° C., and most preferably 400° C. to 525° C., a gas hourly space velocity of 10,000 $hr^{-1}$ or more. Embodiment 14 is the method of any one of embodiments 11 to 13, wherein $C_2+$ hydrocarbon selectivity is at least 60%, 60% to 80%, or 60% to 70%. Embodiment 15 is the method of embodiment 14, wherein the $O_2$ conversion is at least 90%. Embodiment 16 is the method of embodiment 14, further including contacting the first product stream with a second catalyst that is capable of catalyzing an oxidative coupling of methane reaction to produce a second product stream that includes $C_2+$ hydrocarbons, wherein the amount of $C_2+$ hydrocarbons in the second product stream is greater than the amount of $C_2+$ hydrocarbons in the first product stream, wherein the second catalyst is positioned downstream from the first catalyst. Embodiment 17 is the method of embodiment 16, wherein the average temperature of the reactant feed just prior to or during contact with the metal oxide catalyst is 275° C. to less than 700° C., preferably 300° C. to 550° C., or more preferably 300° C. to 450° C. Embodiment 18 is the method of embodiment 17, wherein heat produced during the oxidative coupling of methane reaction between the reactant feed and the metal oxide catalyst is at least partially used to heat the first product stream. Embodiment 19 is the method of embodiment 19, wherein the average temperature of the first product stream is at least 700° C., preferably 700° C. to 1000° C., or more preferably 700° C. to 900° C. just prior to or during contact with the second catalyst. Embodiment 20 is the method of any one of embodiments 16 to 19, wherein the first product stream, prior to being contacted with the second catalyst, is contacted with an oxygen gas feed. Embodiment 21 is the method of any one of embodiments 16 to 20, wherein the second product stream is contacted with an oxygen gas feed. Embodiment 22 is the method of any one of embodiments 17 to 22, wherein the second catalyst is a supported catalyst. Embodiment 23 is the method of embodiment 22, wherein the support is silicone dioxide, lanthanum oxide, or aluminum oxide, or a combination thereof. Embodiment 24 is the method of any one of embodiments 16 to 23, wherein the second catalyst is a bulk metal catalyst. Embodiment 25 is the method of any one of embodiments 22 to 24, wherein the second catalyst includes manganese or a compound thereof, tungsten or a compound thereof, lanthanum or a compound thereof, sodium or a compound thereof, cerium or a compound thereof, silicon or a compound thereof, and any combination thereof. Embodiment 26 is the method of embodiment 25, wherein the second catalyst is a supported catalyst that includes $Mn-Na_2WO_4/SiO_2$. Embodiment 27 is the method of any one of embodiments 16 to 26, wherein $C_{2+}$ hydrocarbon selectivity is at least 70%, preferably 70% to 95%, and most preferably 75% to 90%. Embodiment 28 is the method of embodiment 27, wherein $O_2$ conversion is at least 95% or is 100%, and $CH_4$ conversion is at least 15%, or 15% to 35%, or 20% to 35%. Embodiment 29 is the method of any one of embodiments 16 to 28, wherein the reaction occurs in a continuous flow reactor. Embodiment 30 is the method of embodiment 29, wherein the continuous flow reactor is a fixed-bed reactor or a fluidized reactor.

Embodiment 31 is a system for producing $C_2+$ hydrocarbons. The system includes (a) an inlet for a reactant feed containing methane and oxygen; (b) a reaction zone that is configured to be in fluid communication with the inlet, wherein the reaction zone includes any one of the metal oxide catalysts of embodiments 1 to 11; and (c) an outlet configured to be in fluid communication with the reaction zone and configured to remove a first product stream including $C_2+$ hydrocarbons from the reaction zone. Embodiment 32 is the system of embodiment 31, wherein the reaction zone further includes the reactant feed and the first product stream. Embodiment 33 is the system of embodiment 32, wherein the temperature of the reactant feed is less than 700° C., preferably 275° C. to less than 700° C., more preferably 400° C. to 550° C., and most preferably 425° C. to 525° C. Embodiment 34 is the system of any one of embodiments 31 to 33, further including a collection device that is capable of collecting the first product stream. Embodiment 35 is the system of embodiments 31 or 33, wherein the reaction zone further includes a second catalyst that is capable of catalyzing an oxidative coupling of methane reaction, the second catalyst being positioned downstream from the metal oxide catalyst. Embodiment 36 is the system of embodiments 31 to 35, wherein the system is configured such that the first product stream obtained from an oxidative coupling of methane reaction between the reactant feed and the metal oxide catalyst is contacted with the second catalyst to produce a second product stream that includes $C_2+$ hydrocarbons, wherein the amount of $C_2+$ hydrocarbons in the second product stream is greater than the amount of $C_2+$ hydrocarbons in the first product stream. Embodiment 37 is the system of embodiment 36, wherein the outlet is positioned downstream from the second catalyst and is configured to remove the second product stream from the reaction zone. Embodiment 38 is the system of any one of embodiments 36 to 37, wherein the system is configured such that the average temperature of the reactant feed at the inlet or just prior to or during contact with the metal oxide catalyst is 275° C. to less than 700° C., preferably 300° C. to 550° C., or more preferably 300° C. to 450° C. Embodiment 39 is the system of embodiment 38, wherein the system is configured such that the temperature of the first product stream is at least 700° C., preferably 700° C. to 1000° C., or more preferably 700° C. to 900° C. just prior to or during contact with the second catalyst. Embodiment 40 is the system of any one of embodiments 36 to 39, wherein the system further includes a second inlet that is positioned upstream from the outlet and is configured to introduce an oxygen gas feed to the (i) first product stream prior to contacting the second catalyst or (ii) second product stream. Embodiment 41 is the system of embodiment 40, wherein the second catalyst is a supported catalyst. Embodiment 42 is the system of embodiment 41, wherein the support is silicone dioxide, lanthanum oxide, or aluminum oxide, or a combination thereof.

Embodiment 43 is the system of embodiment 42, wherein the second catalyst is a bulk metal oxide catalyst. Embodiment 44 is the system of any one of embodiments 40 to 43, wherein the second catalyst includes manganese or a compound thereof, tungsten or a compound thereof, lanthanum or a compound thereof, sodium or a compound thereof, cerium or a compound thereof, silicon or a compound thereof, and any combination thereof. Embodiment 45 is the system of embodiment 44, wherein the second catalyst is a supported catalyst including $Mn$—$Na_2WO_4/SiO_2$. Embodiment 46 is the system of any one of embodiments 40 to 45, wherein the reaction zone is a continuous flow reactor. Embodiment 47 is the system of embodiment 46, wherein the continuous flow reactor is a fixed-bed reactor, a fluidized reactor, or a moving bed reactor.

Embodiment 48 is a method of making a metal oxide catalyst of any one of embodiments 1 to 11. The method includes (a) obtaining a solution including lanthanum nitrate and cerium salts, wherein the molar ratio of La to Ce is 1<La:Ce<30; (b) heating the aqueous mixture to remove the water to obtain a dried material; and (c) calcining the dried material at a temperature of 400 to 675° C. for a sufficient period of time to obtain the metal oxide catalyst of any one of embodiments 1 to 11. Embodiment 49 is the method of embodiment 48, wherein the sufficient period of time ranges between 1 and 24 hours, preferably 3 and 12 hours, and most preferably 4 and 8 hours. Embodiment 50 is the method of embodiment 48, wherein the molar ratio of La to Ce is 5<La:Ce<30, or 5<La:Ce<15.

The terms "about" or "approximately" are defined as being close to as understood by one of ordinary skill in the art, and in one non-limiting embodiment the terms are defined to be within 10%, preferably within 5%, more preferably within 1%, and most preferably within 0.5%.

The term "bulk metal oxide catalyst" as that term is used in the specification and/or claims, means that the catalyst includes at least one metal, and does not require a carrier or a support.

The terms "$C_x+$ hydrocarbons" where x is an integer refers to a mixture of hydrocarbons having a carbon number of x and more. For example $C_2+$ hydrocarbons is a mixture of hydrocarbons having 2 and more carbon numbers.

The term "substantially" and its variations are defined as being largely but not necessarily wholly what is specified as understood by one of ordinary skill in the art, and in one non-limiting embodiment substantially refers to ranges within 10%, within 5%, within 1%, or within 0.5%.

The terms "inhibiting" or "reducing" or "preventing" or "avoiding" or any variation of these terms, when used in the claims and/or the specification includes any measurable decrease or complete inhibition to achieve a desired result.

The term "effective," as that term is used in the specification and/or claims, means adequate to accomplish a desired, expected, or intended result.

The terms "wt. %" or "vol. %" refers to a weight or volume percentage of a component, respectively, based on the total weight or the total volume of material that includes the component. In a non-limiting example, 10 grams of metal in 100 grams of the catalyst is 10 wt. % of metal.

The use of the words "a" or "an" when used in conjunction with the term "comprising" in the claims or the specification may mean "one," but it is also consistent with the meaning of "one or more," "at least one," and "one or more than one."

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The catalysts of the present invention can "comprise," "consist essentially of," or "consist of" particular ingredients, components, compositions, etc. disclosed throughout the specification. With respect to the transitional phase "consisting essentially of," in one non-limiting aspect, a basic and novel characteristic of the catalysts of the present invention are their abilities to catalyze oxidative coupling of methane at lower temperatures (e.g., 700° C. or less).

Other objects, features and advantages of the present invention will become apparent from the following figures, detailed description, and examples. It should be understood, however, that the figures, detailed description, and examples, while indicating specific embodiments of the invention, are given by way of illustration only and are not meant to be limiting. Additionally, it is contemplated that changes and modifications within the spirit and scope of the invention will become apparent to those skilled in the art from this detailed description.

While the invention is susceptible to various modifications and alternative forms, specific embodiments thereof are shown by way of example in the drawings and may herein be described in detail. The drawings may not be to scale.

DETAILED DESCRIPTION OF THE INVENTION

The currently available catalysts used in oxidative coupling of methane reactions to produce hydrocarbons having two or more carbon atoms ($C_2+$ hydrocarbons) are prone to sintering and coking, both of which can lead to inefficient catalyst performance and ultimately failure of the catalyst after relatively short periods of use. This can lead to inefficient $C_2+$ hydrocarbon production as well as increased costs associated with their production. Further, current technology require the feed to be heated to elevated temperatures (e.g., greater than 750° C.) prior to contacting the catalyst to initiate (e.g., ignite) and maintain the oxidative coupling reaction.

A discovery has been made that avoids the coking and sintering described above and lowers the average ignition temperature of the exothermic oxidative coupling reaction. The discovery is premised on the use of a bulk metal catalyst that includes a $La(OH)_3$ crystal phase in a La—Ce oxide catalyst. This catalyst can catalyze the oxidative coupling of methane at milder conditions than conditions being used with currently available catalysts. The La—Ce oxide catalyst with $La(OH)_3$ has structural characteristics that are believed to provide for an environment that has both high oxygen capacity and mobility characteristics thereby promoting ignition at lower temperatures (e.g., less than 700° C.) and to produce $C_2$ and/or higher hydrocarbons at higher selectivities.

These and other non-limiting aspects of the present invention are discussed in further detail in the following sections.
A. Catalytic Material
1. First/Upstream Catalytic Material The metals that can be used in the context of the present invention to create bulk metal oxides or supported catalysts include at least two metals ($M^1$ and $M^2$) from the lanthanide series (Group IIIB, Column 3) of the Periodic Table. The metals or metal compounds can be purchased from any chemical supplier such as Sigma-Aldrich, Alfa-Aeaser, Strem, etc. Lanthanides metals and metal compounds include lanthanum, cerium, praseodymium (Pr), neodymium (Nd), promethium (Pm), terbium (Tb), dysprosium (Dy), holmium (Ho), erbium (Er), thulium (Tm), lutetium (Lu) or any combination thereof, with lantheum and cerium oxides being preferred. In a particular embodiment, the catalyst does not contain a dopant. In a preferred embodiment, the catalyst consists essentially of lanthanum-cerium oxide and lanthanum hydroxide. In a non-limiting example, lanthanum nitrate and cerium nitrate are used in combination to create the catalysts of the present invention.

The catalysts are crystalline in structure and can include one or more crystalline phases. The phases can have a common crystal framework and structure. At least one phase contains a trinary structure of two metals and oxygen ($M^1M^2O$) where at least one of $M^1$ and $M^2$ is in a trivalent state. For example, the metal oxide catalyst can be La—Ce oxides, where La is in the trivalent state (III).

A second phase is a $M^1(OH)_3$ crystal phase, where $M^1$ is the trivalent ion of the $M^1M^2O$ compound, (e.g., lanthanum). In the most preferred embodiment, $M^1$ is lanthanum and the second phase is $La(OH)_3$. The $M^1(OH)_3$ crystal phase is believed to have a hexagonal crystal structure and that the $M^1(OH)_3$ (e.g., $La(OH)_3$) is incorporated in the $M^1M^2O$ (e.g., La—Ce oxide) crystal lattice.

The bulk metal oxide catalysts of the present invention can be made by processes that provide a crystalline structure as exemplified in the Examples section. A non-limiting example includes dissolving salts of lantheum and cerium (for example, $La(NO_3)_3$ and $Ce(NO_3)_3$) in de-ionized water with agitation. The metal salts can be in a 2:1 to 30:1 molar ratio, preferably a 5:1 to 30:1, or most preferably a 5:1 to 15:1 molar ratio, of $M^1:M^2$ (for example, $La(NO_3)_3$ and $Ce(NO_3)_3$). The molar ratio of $M^1$ to $M^2$ (e.g., La:Ce) can be greater than 1, or 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30 or any value there between. In a particular instance, the $M^1$ to $M^2$ (e.g., La:Ce) molar ratio is from 5 to 30, 5 to 15, or 7 to 12. The aqueous mixture of the salts can be dried at a temperature from 110° C. to 130° C., for example, 125° C. The dried material can be calcined by heating the pellets to an average temperature between 400° C. and 850° C., 500° C. to 700° C., with 600° C. and 650° C. being preferred, at a rate of about 1° C. per minute and holding at between 600° C. and 650° C. for 3 to 12 hours, or 4 to 8 hours, and then cooled at a rate of about 1° C. per minute to ambient temperature (about 72 to 80° C.). In a preferred aspect of the invention, the calcining temperature is 650° C. at 4 to 8 hours. The resulting catalyst has discrete $M^1(OH)_3$ (e.g., $La(OH)_3$) phase in the crystal lattice). In a preferred embodiment, the La—Ce oxide has $La(OH)_3$ incorporated in its crystal lattice.

The bulk metal oxide catalysts of the present invention can be put on a support. Supported metal oxide catalysts of the present invention can be made by generally known catalyst preparation techniques. The support can be $Al_2O_3$, $SiO_2$ or other materials. In some embodiments, the support may be combined with the catalytic metal to form a catalyst (for example, an incipient impregnation technique). In a particular embodiment, the catalyst is not a nanowire or present in a nanowire substrate. As illustrated in the Examples section, the produced bulk metal oxide catalysts of the invention are coke resistant materials at elevated temperatures, such as those typically used in oxidative coupling of methane reactions (e.g., 400° C. up to 1000° C. or range from 400° C., 450° C., 500° C., 525° C., 550° C., 600° C., 700° C., 750° C., to 950° C.). Further, the produced catalysts can be used effectively in oxidative coupling reactions of methane at an average temperature range from 275° C. up to 1000° C. or from 400° C. to 525° C., at a gas hourly space velocity (GHSV) range from 500 to 100,000 $h^{-1}$ or more at atmospheric or elevated pressures, preferably a temperature of 400° C. to 525° C. and a GHSV of 50,000 $h^{-1}$ or more. The metal oxide catalyst can have a $C_2+$ hydrocarbon selectivity of at least 60%, 60% to 80%, or 60% to 70%, or at least 60%, 65%, 70%, 75%, 80% or any range there between. The metal oxide catalyst can have $O_2$ conversion of at least 90% or 100%.

2. Additional Catalytic Material

Additional catalysts can be used in combination with the catalyst of the present invention. The additional catalysts (e.g., a second catalyst, third catalyst, fourth catalyst, etc.) can be positioned downstream of the catalyst (first catalyst). The second catalyst can be the same catalysts, different catalysts, or a mixture of catalysts. The catalysts can be supported, bulk metal catalysts, or unsupported catalysts. The support can be active or inactive. The catalyst support can include MgO, $Al_2O_3$, $SiO_2$, or the like. All of the support materials can be purchased or be made by processes known to those of ordinary skill in the art (e.g., precipitation/co-precipitation, sol-gel, templates/surface derivatized metal oxides synthesis, solid-state synthesis, of mixed metal oxides, microemulsion technique, solvothermal, sonochemical, combustion synthesis, etc.). One or more of the catalysts can include one or more metals or metal compounds thereof. Catalytic metals include Li, Na, Ca, Cs, Mg, La, Ce, W, Mn, Ru, Rh, Ni, and Pt. Non-limiting examples of catalysts of the invention include La on a MgO support, Na, Mn, and $La_2O_3$ on an aluminum support, Na and Mn oxides on a silicon dioxide support, $Na_2WO_4$ and Mn on a silicon dioxide support, or any combination thereof. Non-limiting examples of catalysts that promote oxidative coupling of methane to produce ethylene are $Li_2O$, $Na_2O$, $Cs_2O$, MgO, $WO_3$, $Mn_3O_4$, or any combination thereof. A non-limiting example of a mixture of catalysts is a catalyst mixture that includes a supported catalyst containing Ni, Ce and La, and another supported catalyst containing Mn, W, and Na (e.g., Mn—$Na_2WO_4$ on $SiO_2$). In some instances, the second catalyst has a $C_2$+ selectivity that is greater than the first catalyst.

B. Reactants

The reactant mixture in the context of the present invention is a gaseous mixture that includes, but is not limited to, a hydrocarbon or mixtures of hydrocarbons and oxygen. The hydrocarbon or mixtures of hydrocarbons can include natural gas, liquefied petroleum gas containing of $C_2$-$C_5$ hydrocarbons, $C_6$+ heavy hydrocarbons (e.g., $C_6$ to $C_{24}$ hydrocarbons such as diesel fuel, jet fuel, gasoline, tars, kerosene, etc.), oxygenated hydrocarbons, and/or biodiesel, alcohols, or dimethyl ether. In a preferred aspect, the hydrocarbon is a mixture of hydrocarbons that is predominately methane (e.g., natural gas). The oxygen containing gas used in the present invention can be air, oxygen enriched air, oxygen gas, and can be obtained from various sources. The reactant mixture may further contain other gases, provided that these do not negatively affect the reaction. Examples of such other gases include carbon dioxide, nitrogen and hydrogen. The hydrogen may be from various sources, including streams coming from other chemical processes, like ethane cracking, methanol synthesis, or conversion of methane to aromatics. Carbon dioxide may be from natural gas, or a waste or recycle gas stream (e.g. from a plant on the same site, like for example from ammonia synthesis) or after recovering the carbon dioxide from a gas stream.

C. Oxidative Coupling of Methane Process

In one particular aspect of the invention, a method of producing ethylene from a reaction mixture that includes methane ($CH_4$) and an oxygen ($O_2$) containing gas is described. The reaction mixture can be contacted with the metal oxide catalyst of the present invention under sufficient conditions to produce a product stream (e.g., a first product stream) that includes ethylene. The ethylene is obtained from oxidative coupling of $CH_4$. In some instances, continuous flow reactors can be used in the context of the present invention to treat methane with oxygen to produce ethylene. Non-limiting examples of continuous flow reactors include a fixed-bed reactor, a fluidized reactor, a stacked bed reactor, an ebullating bed reactor, or a moving bed reactor. The reactors include conventional components for controlling chemical reactions such as, for example, heating elements, thermocouples, manual and/or automated controllers, valves, and the like. The reactors can be jacketed or unjacketed. Jacketed reactors can be capable of circulating a heat exchange fluid for addition or removal of heat as necessary during the chemical reaction. In some aspects of the present invention, the reactant mixture can have a molar ratio of $CH_4$ to $O_2$ ranges from 0.3 to 20, 0.5 to 15, 1 to 10, or 5 to 7.5 or any range there between. The molar ratio of $CH_4$ to $O_2$ can be 0.3, 0.5, 1, 1.5, 2, 2.5, 3, 3.5, 4, 4.5, 5, 5.5, 6, 6.5, 7, 7.5, 8, 8.5, 9, 9.5, 10, 15, or 20 or any value there between. Process conditions to effect production of ethylene from methane through oxidative coupling can include an average temperature of less than 1000° C., less than 700° C., 275° C. to 700° C., 400 to 550° C. or from 425 to 525° C. and a pressure of about 1 bara, and/or a gas hourly space velocity (GHSV) from 500 to 50,000 h$^{-1}$ or more. In a preferred embodiment, the reactant mixture is heated to an average temperature of less than 700° C., preferably 275° C. to 700° C., more preferably 300° C. to 550° C. or most preferably from 300° C. to 450° C. In some embodiments, the metal oxide catalyst and the reactant mixture are heated to the same temperature and the temperature downstream of the metal oxide catalyst is maintained at a different temperature. Severity of the process conditions may be manipulated by changing, the hydrocarbon source, oxygen source, carbon dioxide source, pressure, flow rates, the temperature of the process, the catalyst type, and/or catalyst to feed ratio. A process in accordance with the present invention is carried out at pressures more than atmospheric pressure.

In some embodiments, the catalyst is used in combination with the second catalyst described above that is capable of catalyzing an oxidative coupling of methane reaction to produce a second product stream that includes $C_2$+ hydrocarbons. Such a combination produces a greater amount of $C_2$+ hydrocarbons in the second product stream than those produced in the first product stream. The second catalyst can be positioned downstream from the first catalyst. When the metal oxide catalyst of the present invention (first catalyst) is used in combination with the second catalyst and positioned upstream from the second catalyst, the reactant feed can be at a lower average temperature relative to average temperatures conventionally used for oxidative coupling of methane. In some instances, the average temperature of the reactant feed just prior to or during contact with the first catalyst is 275° C. to less than 700° C., 300 to 550° C., or preferably 300° C. to 450° C. at a GHSV of 500 to 10,000 h$^{-1}$. In some embodiments, the feed can be heated to the same temperature as the first reaction zone. Heat generated during the oxidative coupling of methane between the reactant feed and the first catalyst can be used to heat the first product stream. The use of a catalyst that can ignite the oxidative coupling of methane at relatively low temperature in combination with another catalyst allows for higher $C_2$+ yield while extending catalyst life by inhibiting sintering of catalytic metals and/or agglomeration of particles in the catalyst.

Figure 1:
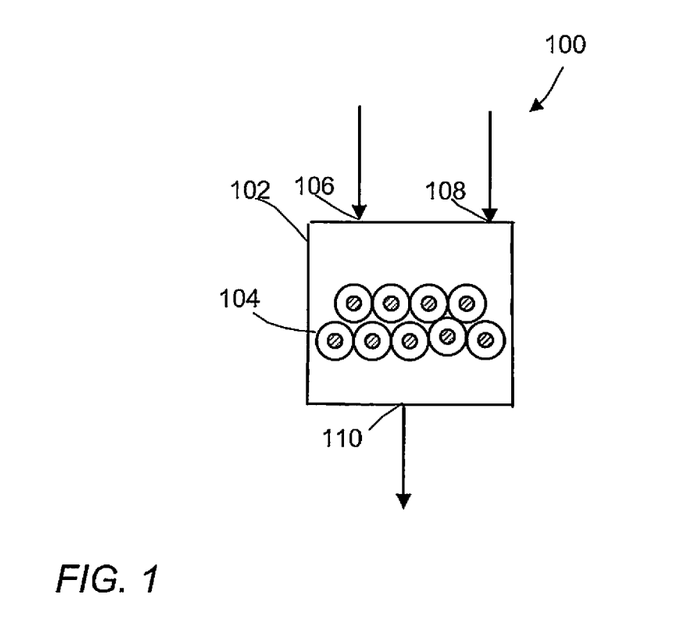
FIG. 1 is a schematic of an embodiment of a system to produce ethylene using the catalytic material of the present invention.

Referring to FIG. 1, a schematic of system 100 for the production of ethylene is depicted. System 100 may include a continuous flow reactor 102 and a catalytic material 104. In a preferred embodiment, catalytic material 104 is the La—Ce oxide catalytic material of the present invention. A reactant stream that includes methane can enter the continuous flow reactor 102 via the feed inlet 106. An oxygen containing gas (oxidant) is provided in via oxidant source inlet 108. In some aspects of the invention, methane and the oxygen containing gas are fed to the reactor via one inlet. The reactants can be provided to the continuous flow reactor 102 such that the reactants mix in the reactor to form a reactant mixture prior to contacting the catalytic material 104. The average temperature of reactant mixture prior to contacting the catalytic material is less than 1000° C., or 275° C., 300° C. to 700° C., 450° C. to 550° C., or 400° C. to 525° C. or any range there between. In some embodiments, the catalytic material is heated to an average temperature of less than 1000° C., or 275° C., 300° C. to 700° C., 450° C. to 550° C., or 400° C. to 525° C. or any range there between. The average temperature of the reactant mixture, the catalytic material, or both can be 300° C., 325° C., 350° C., 375° C., 400° C., 425° C., 450° C., 475° C., 500° C., 525° C., 550° C., 600° C., 625° C., 650° C., or 700° C. In some instances, the catalytic material 104 may be layered in the continuous flow reactor 102. Contact of the reactant mixture with the first catalytic material 104 produces a product stream (for example, ethylene and generates heat (i.e., an exotherm or rise in temperature is observed). After ignition, the reaction conditions are maintained downstream of the first catalyst at temperatures sufficient to promote continuation of the process. Wishing not to be bound by theory, it is believed that the product stream from contact of the feed stream with the catalytic material in the presence of oxygen at lower average temperatures does not generate excessive heat, thus only a small amount or substantially no carbon dioxide or carbon monoxide is formed resulting in a relatively high $C_2+$ selectivity. The product stream can exit continuous flow reactor 102 via product outlet 110.

Figure 2A:
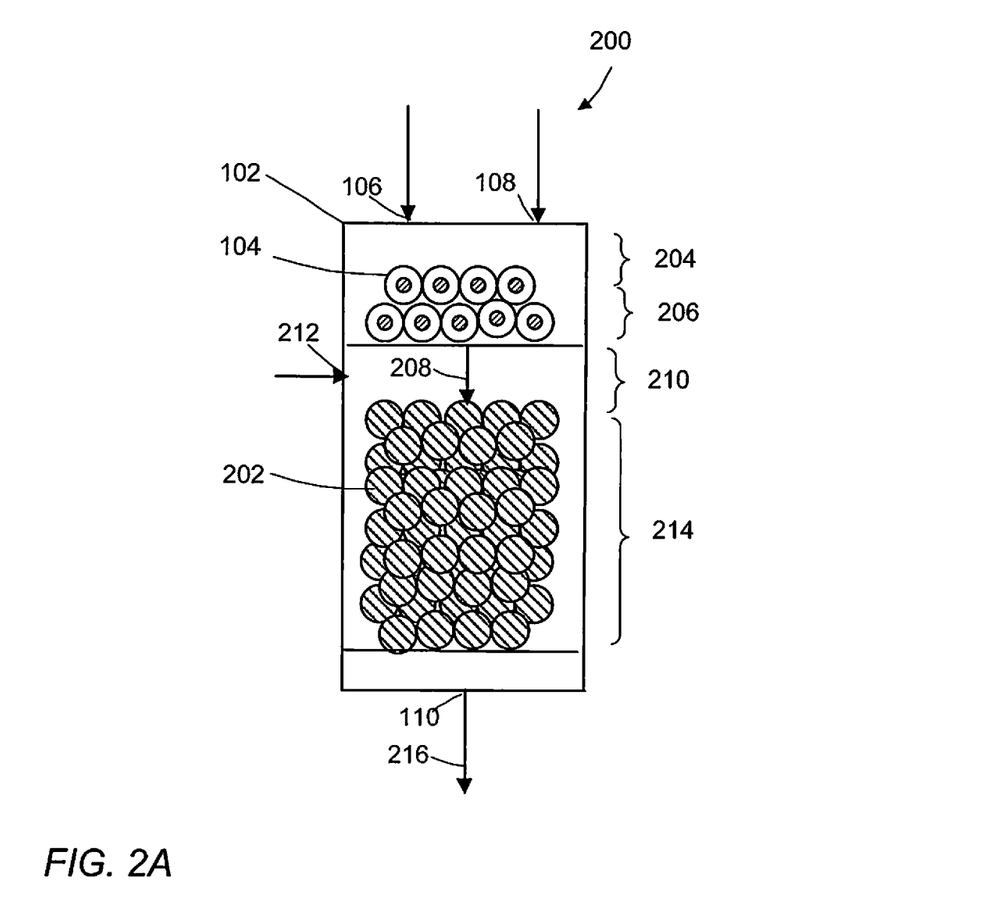
FIGS. 2A and 2B are schematics of embodiments of a system to produce ethylene using the catalytic material of the present invention and an additional catalyst.
Figure 2B:
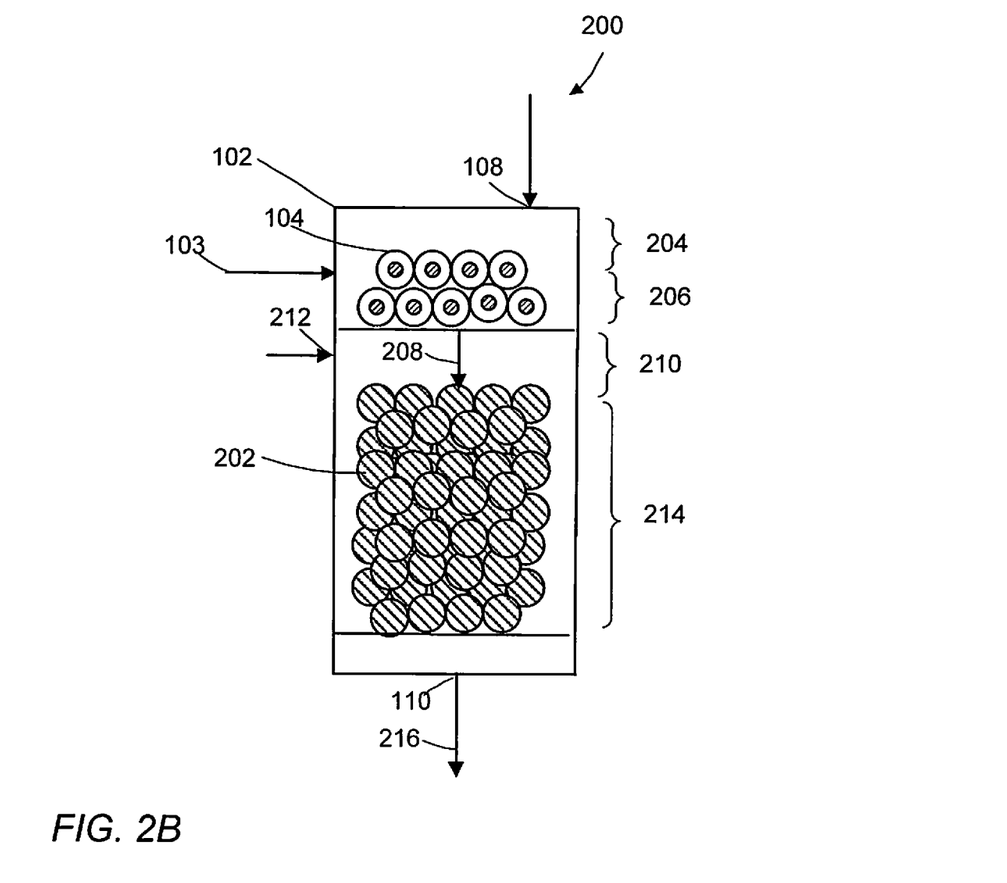

Referring to FIGS. 2A and 2B, a schematic of system 200 having the catalyst of the present invention and a second catalyst is described for the production of ethylene. System 200 may include a continuous flow reactor 102, a first catalytic material 104, and a second catalytic material 202 positioned downstream of the first catalytic material. The first catalytic material 104 can be the catalytic material of the present invention and second catalytic material 202 can the same or different as catalytic material 104. In a preferred embodiment, second catalytic material 202 is a catalytic material that has a higher $C_2+$ selectivity than the first catalytic material 104. A reactant stream that contains methane enters the continuous flow reactor 102 via the feed inlet 106. An oxygen containing gas is provided in via oxidant source inlet 108. The reactants can be provided to the continuous flow reactor 102 such that the reactants mix in the zone 204 to form a reactant mixture prior to contacting the first catalytic layer 104. In some embodiments, the reactants can be provided to the continuous flow reactor 102 are provided as one stream via one inlet. As shown in FIG. 2B, a mixture of methane (e.g., hydrocarbon gas) and an oxygen containing gas can enter continuous flow reactor via inlet 103 and an additional oxygen containing gas can be added via oxidant inlet 108. The average temperature of the reactant mixture in zone 206 prior to contacting the catalytic material is less 1000° C., or 275° C., 300° C. to 700° C., 450° C. to 550° C., or 400° C. to 525° C. or any range there between. The GHSV can be adjusted to, or be maintained at, 500 hr$^{-1}$ or more. In some embodiments, the reaction zone 206 and/or catalytic material 104 is heated to an average temperature of less than 1000° C., or 275° C., 300° C. to 700° C., 450° C. to 550° C., or 400° C. to 525° C. or any range there between. Contact of the reactant mixture with the first catalytic material 104 in reaction zone 206 produces a first product stream 208 (for example, ethylene and generates heat (i.e., an exotherm or rise in temperature is observed). The first product stream 208 can include unreacted methane, oxygen containing gas, and $C_2+$ hydrocarbons. A portion of the generated heat in reaction zone 206 is transferred to the first product stream 208. In a preferred embodiment, the first product stream 208 is heated only by heated generated from contact of the reactant mixture with the first catalytic material 104. As shown in FIG. 2B, the first catalytic material 104 and second catalytic material 202 are separated with zone 210, however, the two catalytic materials may be positioned such that there is a minimal amount of space between the two catalytic layers. In some embodiments, the amount of oxygen in the oxygen containing gas is monitored, and if more oxygen is necessary, oxygen can be added to zone 210 via oxygen containing gas source inlet 212. In a preferred embodiment, at least 90% or substantially all (e.g., 100%) of the oxygen provided to the reactant mixture is converted, and thus, additional oxygen is provided via oxidant inlet 212 to zone 210. The first product stream 208 can be heated prior to and during contact with the second catalytic material 202. In a preferred embodiment, heat from reaction zone 206 heats the first product stream and/or the oxygen containing gas to a temperature of at least 700° C., or 700° C. to 1000° C., 700° C. to 900° C. The heated product steam with sufficient oxygen either remaining in the stream or from an external source (e.g., from the oxygen containing gas entering via inlet 212 shown in FIG. 2B) can enter reaction zone 214. The reaction zone 214 can be heated to an average temperature of at least 700° C., or 700° C. to 1000° C., 700° C. to 900° C. by the heat generated in zone 206 and/or by the heat generated in zone 214. The GHSV can be adjusted to, or be maintained at, a rate higher than the first reaction zone (e.g., 5,000 hr$^{-1}$ or more, 10,000 hr$^{-1}$ or more, 20,000 hr$^{-1}$ or more, 50,000 hr$^{-1}$ or more, 60 hr$^{-1}$ or more, or 80,000 hr$^{-1}$ or more, preferably higher than 50,000 hr$^{-1}$). Contact of the heated first product stream 208 with the second catalytic material in the presence of oxygen in reaction zone 214 generates a second product stream 216. In some embodiments, contact of the reactant mixture with the first catalyst is controlled such that the methane conversion is greater than zero, but as low as possible. Said another way, the reaction is started using the first catalyst and then maintained using the second catalytic material. Use of an igniting catalyst and a high selectivity catalyst can provide high selectivities to $C_2+$ hydrocarbon with prolonged catalyst life (e.g., sintering and coking of the catalyst are minimized). Second product stream 216 can have more $C_2+$ hydrocarbons than the first product stream 206. The second product stream 216 can exit continuous flow reactor 102 via product outlet 110. While only two layers of catalytic material is described it should be understood that additional catalysts can be positioned downstream of the second catalytic material to achieve the desired $C_2+$ hydrocarbons. The additional catalysts can be any of the catalysts described throughout the invention.

The resulting $C_2+$ hydrocarbons and water produced from the systems of the invention (for example, systems 100 and 200) can be collected in a collection device and/or transported via piping to separation unit. In the separation unit, the $C_2+$ hydrocarbons are separated using known separation techniques, for example, distillation, absorption, membrane technology to produce an ethylene product. In embodiments when carbon dioxide is in the reactant mixture and/or generated in situ, the resulting gases (for example, CO, $H_2$, and ethylene) produced from the systems of the invention (for example, systems 100 and 200) is separated from the hydrogen, carbon monoxide, and carbon dioxide (if present) using known separation techniques, for example, a hydrogen selective membrane, a carbon monoxide selective membrane, a carbon dioxide selective membrane, or cryogenic distillation to produce one or more products such as ethylene, carbon monoxide, carbon dioxide, hydrogen or mixtures thereof. The separated or mixture of products can be used in additional downstream reaction schemes to create additional products or for energy production. Examples of other products include chemical products such as methanol production, olefin synthesis (e.g., via Fischer-Tropsch reaction), aromatics production, carbonylation of methanol, carbonylation of olefins, the reduction of iron oxide in steel production, etc. The method can further include isolating and/or storing the produced gaseous mixture or the separated products.

EXAMPLES

The present invention will be described in greater detail by way of specific examples. The following examples are offered for illustrative purposes only, and are not intended to limit the invention in any manner. Those of skill in the art will readily recognize a variety of noncritical parameters which can be changed or modified to yield essentially the same results.

Example 1

Synthesis of Catalysts

All materials for the synthesis of the bulk metal oxide catalysts were obtained from Sigma Aldrich Chemical Company (St. Louis, Mo., USA).

Bulk Metal Oxide Catalyst.

Figure 3:
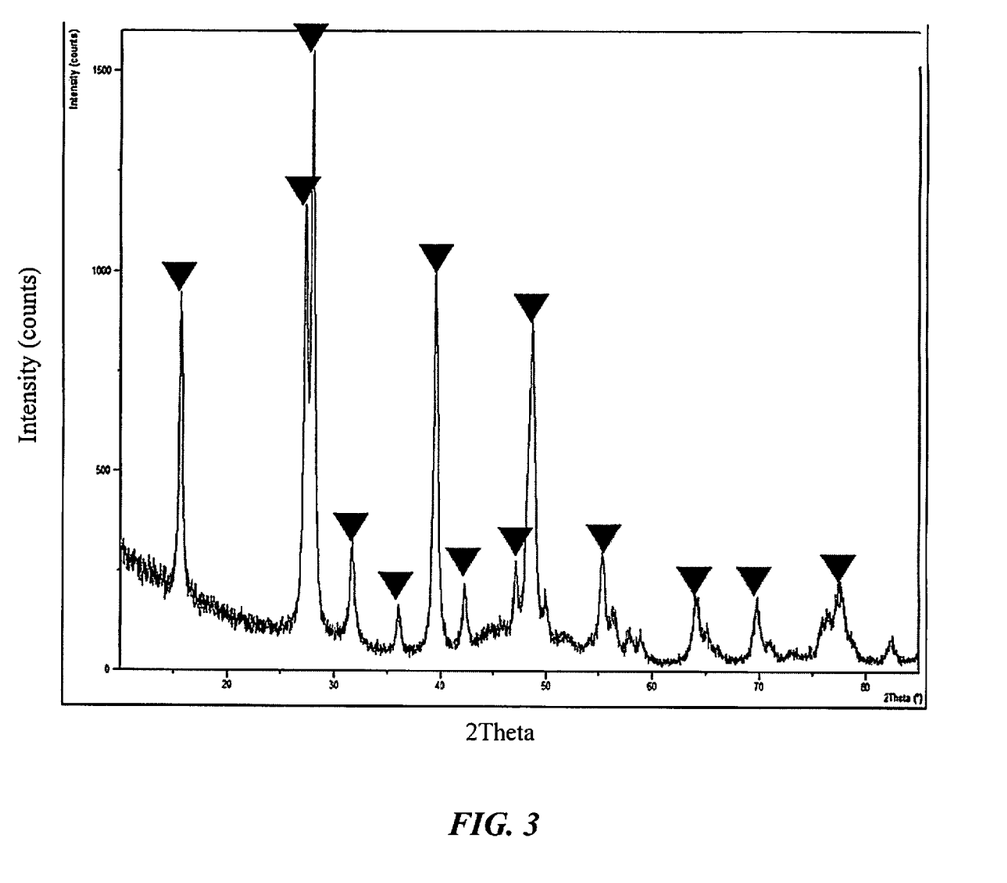
FIG. 3 is an image of an X-Ray Diffraction pattern of catalyst of the present invention having a molar ratio of La:Ce of 15.
Figure 4:
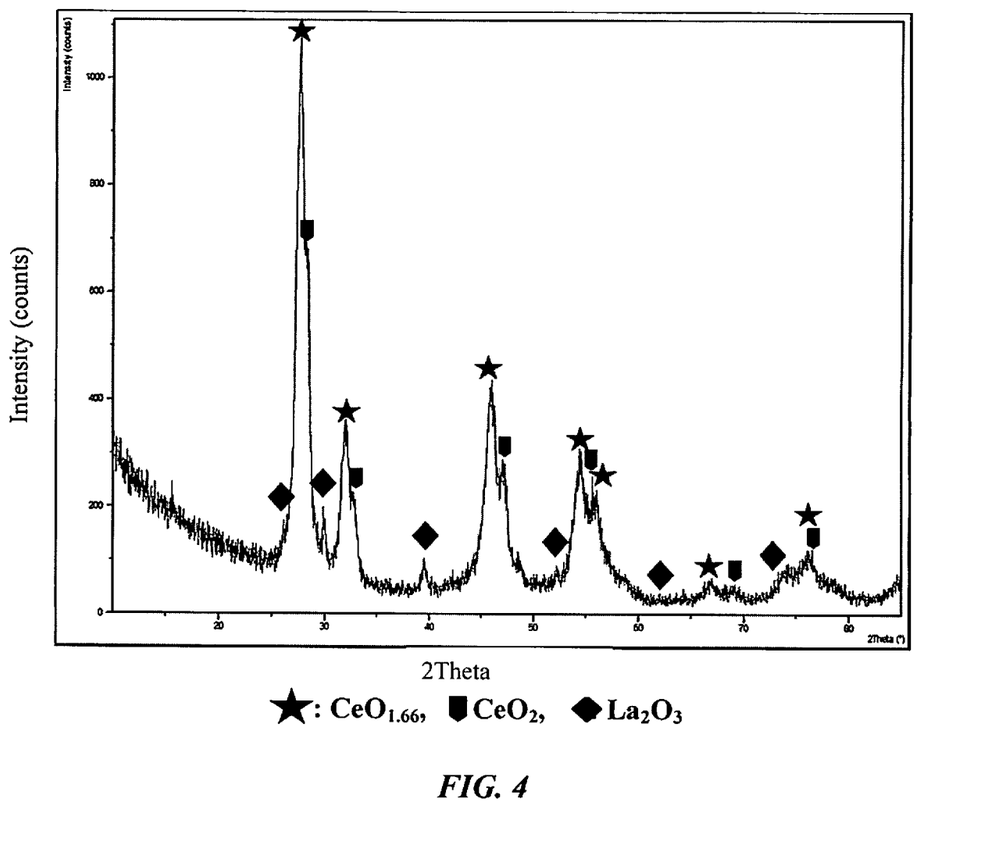
FIG. 4 is an image of X-Ray Diffraction pattern of catalyst having a molar ratio of La:Ce of 1.

Lanthanum nitrate ($La(NO_3)_3$) and cerium nitrate ($Ce(NO_3)_3$) in the molar ratios shown below in Table 1 were dissolved in de-ionized water under agitation. Then the mixture was dried at 125° C. overnight. The dried material was then calcined at 625° C. for 5 hours at a ramp rate of 1° C. per minute. FIG. 3 is an X-Ray Diffraction (XRD) patterns of bulk metal oxide catalyst of the present invention (sample 3 in Table 1) showing the $La(OH)_3$ phase. The upside down triangle indicates the peaks attributable to the $La(OH)_3$. As shown in FIG. 3, the $La(OH)_3$ phase is the dominant phase in the catalyst. FIG. 4 is an X-Ray Diffraction (XRD) patterns of Sample 5 which did not include the $La(OH)_3$ phase.

TABLE 1

| Sample No. | La/Ce (Molar Ratio) | Presence of $La(OH)_3$ Crystal Phase |
|---|---|---|
| 1 | 10 | yes |
| 2 | 30 | yes |
| 3 | 15 | yes |
| 4 | 7 | yes |
| 5 | 1 | no |

Example 2

Oxidative Coupling of Methane

A fixed bed catalyst reactor was filled with a catalytic material of Example 1 (10 mg). The reactor was heated to the required temperature, and a mixture of methane ($CH_4$) and oxygen ($O_2$) at a fixed $CH_4:O_2$ ratio of 7.4 was fed to the reactor at a flow rate of 80 sccm. The ignition temperature, methane conversion, oxygen conversion and selectivity to $C_2^+$ products under 500° C. for each sample are listed in Table 2. Methane conversion was calculated on the basis of difference of inlet and outlet concentrations of methane. Selectivity was calculated on the basis of concentrations of $C_2+$ products in comparison all the converted amount of methane. From analysis of the data, it was concluded that the catalysts containing $La(OH)_3$ crystal phase showed higher $C_2+$ selectivity than the catalyst without the $La(OH)_3$ crystal phase.

TABLE 2

| Sample No. | Ignition Temperature, ° C. | $O_2$ Conversion, % | $CH_4$ Conversion, % | $C_2+$ Selectivity, % |
|---|---|---|---|---|
| 1 | 500 | 98.8 | 15.5 | 67.0 |
| 2 | 450 | 78.2 | 14.2 | 63.1 |
| 3 | 500 | 92.1 | 15.6 | 62.9 |
| 4 | 450 | 99.5 | 16.4 | 68.5 |
| 5 | 450 | 93.9 | 10.6 | 59.5 |

Figure 5:
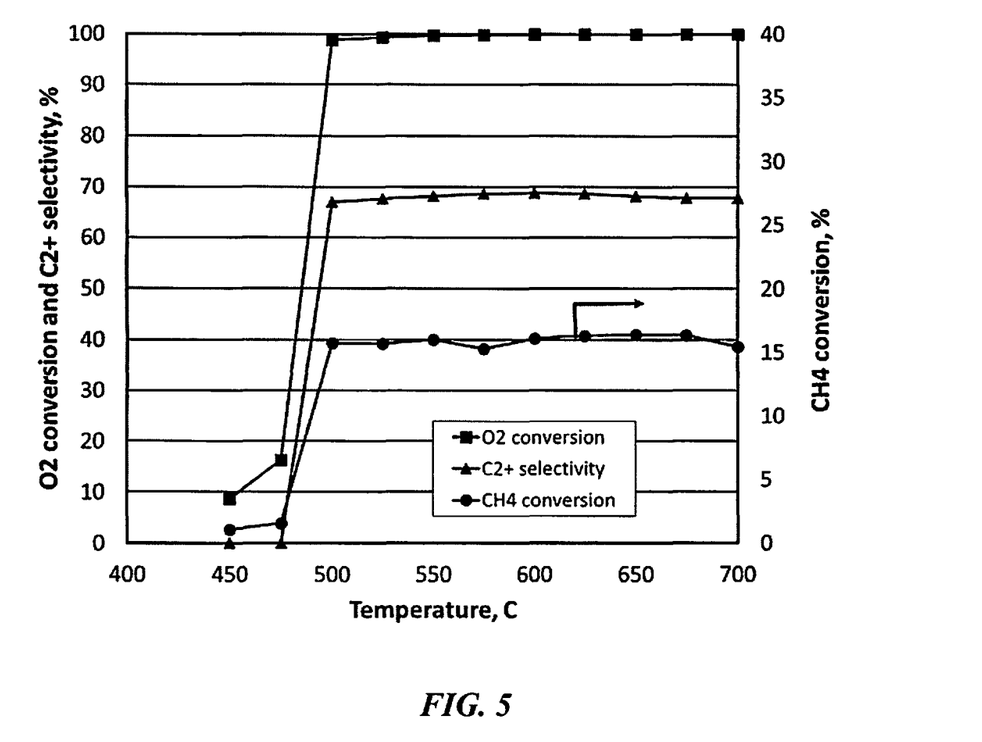
FIG. 5 are graphs of temperature in Celsius versus $O_2$ conversion in percent, $CH_4$ conversion in percent and $C_2+$ selectivity in percent for Sample 1 (La:Ce ratio of 10:1) in an oxidative coupling of methane reaction at a methane to oxygen ratio of 7.4.
Figure 6:
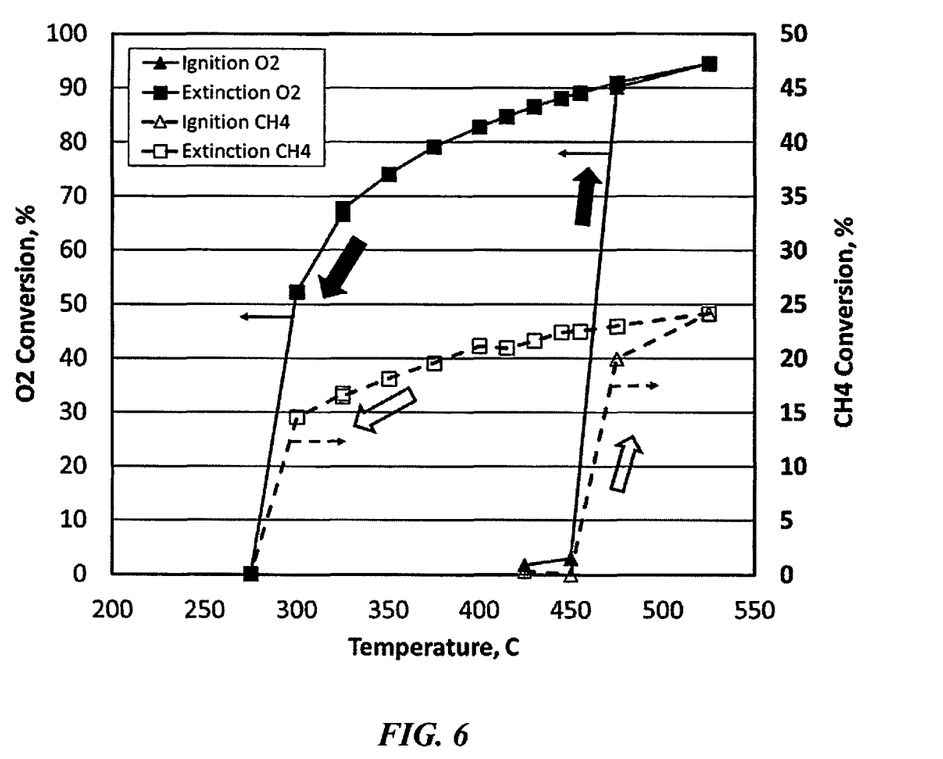
FIG. 6 are graphs of temperature in Celsius versus $O_2$ conversion in percent, $CH_4$ conversion in percent for Sample 3 (La:Ce ratio of 15:1) in an oxidative coupling of methane reaction at a methane to oxygen ratio of 4.

FIG. 5 are graphs of $O_2$ conversion in percent, $CH_4$ conversion in percent and $C_2+$ selectivity in percent versus temperature in Celsius for Sample 1 (La:Ce ratio of 10:1) in an oxidative coupling of methane reaction. From analysis of the data, it was concluded that the reaction ignited at 500° C. FIG. 6 are graphs of $O_2$ conversion in percent, $CH_4$ conversion in percent versus temperature in Celsius for Sample 3 (La:Ce ratio of 15:1) in an oxidative coupling of methane reaction under a methane to oxygen ratio of 4.0. Under these operation conditions, the reaction ignited at about 475° C. It was observed that the reaction extinction temperature under these conditions was 275° C. Thus, a high level of $CH_4$ conversion can be obtained at operation temperature above 275° C.

Example 3

Oxidative Coupling of Methane with Second Catalyst

A fixed bed catalyst reactor was filled with a supported catalyst (100 mg, $MnNa_2WO_4/SiO_2$). The reactor was heated to the required temperature and methane and oxygen was fed to the reactor at a flow rate of 33.3 sccm. The $CH_4:O_2$ ratio, methane conversion, oxygen conversion and with selectivity to $C_2+$ products for each sample is listed in Table 3. Methane conversion was calculated on the basis of difference of inlet and outlet concentrations of methane. Selectivity was calculated on the basis of concentrations of $C_2+$ products in comparison all the converted amount of methane.

TABLE 3

| Sample No. | $CH_4:O_2$ ratio | Reaction Temperature, ° C. | $O_2$ Conversion, % | $CH_4$ Conversion, % | $C_2+$ Selectivity, % |
|---|---|---|---|---|---|
| 6 | 4.0 | 750 | 100 | 30.4 | 73.3 |
| 7 | 7.4 | 800 | 100 | 18.8 | 79.8 |

From analysis of the data in Table 3, the selectivities with the second catalyst in the presence of oxygen were determined to be higher than those obtained from the catalysts used in Example 2.

The invention claimed is:

1. A metal oxide catalyst capable of catalyzing an oxidative coupling of methane reaction, the metal oxide catalyst comprising a lanthanum (La) cerium (Ce) metal oxide and further including a lanthanum hydroxide ($La(OH)_3$) crystalline phase in the crystal lattice of the metal oxide catalyst, wherein the molar ratio of La:Ce is 5<La:Ce<30, and wherein the catalyst is capable of catalyzing the production of $C_2$+ hydrocarbons from methane and oxygen.

2. The metal oxide catalyst of claim 1, wherein the La:Ce is 5<La:Ce<15.

3. The metal oxide catalyst of claim 1, wherein the metal oxide catalyst is a bulk metal oxide catalyst.

4. The metal oxide catalyst of claim 1, wherein the LaCe metal oxide is incorporated into the crystal lattice of the metal oxide catalyst.

5. The metal oxide catalyst claim 1, wherein the metal oxide catalyst is catalyzes the production of $C_2$+ hydrocarbons from methane and oxygen at an average temperature of 400° C. to 550° C.

6. The metal oxide catalyst of claim 5, wherein the metal oxide catalyst has a $C_2$+ hydrocarbon selectivity of at least 60%.

7. The metal oxide catalyst of claim 5, wherein the metal oxide catalyst has an $O_2$ conversion of at least 90%.

8. The metal oxide catalyst of claim 1, wherein the metal oxide catalyst is in contact with a reactant feed that includes methane and an oxygen source.

9. The metal oxide catalyst of claim 8, wherein the reactant feed has an average temperature of less than 1000° C.

10. The metal oxide catalyst of claim 9, wherein at least a portion of the methane in the reactant feed has ignited or has formed into a $C_2$+ hydrocarbon.

11. A method of producing $C_2$+ hydrocarbons from an oxidative coupling of methane reaction, the method comprising contacting a reactant feed that includes methane and an oxygen containing gas with any one of the metal oxide catalysts of claim 1 under conditions sufficient to produce a first product gas stream comprising $C_2$+ hydrocarbons.

12. The method of claim 11, wherein the oxidative coupling of methane reaction occurs at an average temperature of 400° C. to 550° C. and a gas hourly space velocity of 10,000 hr-1 or more.

13. The method of claim 11, wherein $C_2$+ hydrocarbon selectivity is at least 60%.

14. The method of claim 13, wherein the $O_2$ conversion is at least 90%.

15. The method of claim 13, further comprising contacting the first product stream with a second catalyst that is capable of catalyzing an oxidative coupling of methane reaction to produce a second product stream that includes $C_2$+ hydrocarbons, wherein the amount of $C_2$+ hydrocarbons in the second product stream is greater than the amount of $C_2$+ hydrocarbons in the first product stream, wherein the second catalyst is positioned downstream from the first catalyst.

16. The method of claim 15, wherein heat produced during the oxidative coupling of methane reaction between the reactant feed and the metal oxide catalyst is at least partially used to heat the first product stream.

17. The method of claim 16, wherein the average temperature of the first product stream is at least 700° C. just prior to or during contact with the second catalyst.

18. The method of claim 15, wherein the second catalyst comprises manganese or a compound thereof, tungsten or a compound thereof, lanthanum or a compound thereof, sodium or a compound thereof, cerium or a compound thereof, silicon or a compound thereof, and any combination thereof.

19. The method of claim 18, wherein the second catalyst is a supported catalyst comprising $Mn-Na_2WO_4/SiO_2$.

20. A method of making a metal oxide catalyst of claim 1, the method comprising:
obtaining an aqueous solution comprising lanthanum nitrate and cerium salts, wherein the molar ratio of La to Ce is 5<La:Ce<30;
heating the aqueous mixture to remove the water to obtain a dried material; and
calcining the dried material at a temperature of 400 to 675° C. for a sufficient period of time to obtain the metal oxide catalyst.

* * * * *

UNITED STATES PATENT AND TRADEMARK OFFICE
CERTIFICATE OF CORRECTION

| | | |
|---|---|---|
| PATENT NO. | : 10,717,068 B2 | Page 1 of 1 |
| APPLICATION NO. | : 15/579332 | |
| DATED | : July 21, 2020 | |
| INVENTOR(S) | : Wugeng Liang et al. | |

It is certified that error appears in the above-identified patent and that said Letters Patent is hereby corrected as shown below:

On the Title Page

Item (73) Assignee should read:
"SABIC GLOBAL TECHNOLOGIES B.V., Bergen op Zoom (NL)"

Signed and Sealed this
Eighteenth Day of August, 2020

Andrei Iancu
*Director of the United States Patent and Trademark Office*